(12) United States Patent
Kugelmann et al.

(10) Patent No.: US 9,198,830 B2
(45) Date of Patent: Dec. 1, 2015

(54) BAG WITH A FLEXURALLY RIGID PLASTIC PART WELDED INTO IT

(71) Applicant: Fresenius Medical Care Deutschland GmbH, Bad Homburg (DE)

(72) Inventors: Franz Kugelmann, St. Wendel/Bliesen (DE); Joern Hoermann, Heusweiler (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 127 days.

(21) Appl. No.: 13/867,322

(22) Filed: Apr. 22, 2013

(65) Prior Publication Data

US 2013/0281964 A1     Oct. 24, 2013

Related U.S. Application Data

(60) Provisional application No. 61/636,771, filed on Apr. 23, 2012.

(30) Foreign Application Priority Data

Apr. 23, 2012   (DE) .......................... 10 2012 007 904

(51) Int. Cl.
*A61J 1/10*     (2006.01)
*A61J 1/14*     (2006.01)
(Continued)

(52) U.S. Cl.
CPC .... *A61J 1/10* (2013.01); *A61J 1/14* (2013.01); *A61J 1/1462* (2013.01); *A61J 1/1475* (2013.01); *A61M 1/167* (2014.02); *A61M 1/1656* (2013.01);
(Continued)

(58) Field of Classification Search
CPC ............. A61J 1/10; A61J 1/14; A61J 1/1462; A61J 1/16; A61J 1/1475; A61J 1/1481; A61J 1/1487; A61J 2205/30; A61M 1/1656; A61M 1/1666; A61M 1/1668; A61M 1/167; A61M 1/0277; A61M 1/0272; A61M 2209/08; A61M 2209/082; A61M 2209/084; A61M 5/1414; A61M 5/1417; B65D 81/00; B65D 33/007; B65D 33/02; B65D 33/06; B65D 33/14; B65D 57/00; B65D 5/4208; B65D 5/46; B65D 5/46008; B65D 5/46088; B65D 25/28; B65D 43/46; B65D 43/465; B65D 33/1683; B65D 75/5861; B65D 75/5872; B65D 75/5877; Y10S 206/806; Y10S 383/903; Y10S 383/906; Y10S 16/24; Y10S 16/19; Y10S 383/904; A61G 7/0503; A61G 5/10

See application file for complete search history.

(56) References Cited

U.S. PATENT DOCUMENTS 3,558,039 A  *   1/1971   Schmidt ........................... 383/6
3,865,165 A  *   2/1975   Glass ............................ 604/322

(Continued)

FOREIGN PATENT DOCUMENTS

| DE | 24 58 220 | 6/1975 |
|---|---|---|
| DE | 692 01 235 | 8/1995 |
| WO | WO 2007/144427 | 12/2007 |
| WO | WO 2009/052501 | 4/2009 |
| WO | WO 2011/070329 | 6/2011 |

*Primary Examiner* — Adam Marcetich
(74) *Attorney, Agent, or Firm* — Jacobson Holman, PLLC.

(57) ABSTRACT

A bag for receiving, preparing, and producing dialysis fluid has a sealing bordering line and a flexurally rigid hard plastic part connected to the film material. The hard plastic part is connected to the film material separately from the sealing bordering line and offers an area for gripping the bag for fastening it without having to act mechanically on the sealing bordering line in a direct manner.

17 Claims, 2 Drawing Sheets

(51) Int. Cl.
  *A61J 1/16* (2006.01)
  *B65D 33/14* (2006.01)
  *B65D 33/06* (2006.01)
  *B65D 33/16* (2006.01)
  *B65D 33/02* (2006.01)
  *A61M 5/14* (2006.01)
  *A61M 1/16* (2006.01)
  *B65D 81/00* (2006.01)
  *B65D 75/58* (2006.01)

(52) U.S. Cl.
  CPC ........... *A61M 1/1666* (2014.02); *A61M 1/1668* (2014.02); *A61M 5/1414* (2013.01); *A61M 5/1417* (2013.01); *B65D 33/02* (2013.01); *B65D 33/06* (2013.01); *B65D 33/14* (2013.01); *B65D 33/1683* (2013.01); *B65D 81/00* (2013.01); *A61J 1/16* (2013.01); *A61J 2205/30* (2013.01); *A61M 2209/08* (2013.01); *B65D 75/5861* (2013.01); *B65D 75/5872* (2013.01); *B65D 75/5877* (2013.01)

(56) References Cited

U.S. PATENT DOCUMENTS

| | | | |
|---|---|---|---|
| 4,312,352 A * | 1/1982 | Meisch et al. ................ | 604/322 |
| 4,365,629 A * | 12/1982 | Pert et al. ...................... | 604/408 |
| 4,432,763 A * | 2/1984 | Manschot et al. ............ | 604/262 |
| 4,562,984 A * | 1/1986 | Sherlock et al. .............. | 248/95 |
| 4,619,648 A * | 10/1986 | Rath et al. ..................... | 604/326 |
| 4,743,236 A * | 5/1988 | Manschot ...................... | 604/323 |
| 4,869,398 A | 9/1989 | Colvin et al. | |
| 6,428,518 B1 * | 8/2002 | Brengle et al. ................ | 604/191 |
| 2001/0024623 A1 | 9/2001 | Grimm et al. | |
| 2003/0080126 A1 | 5/2003 | Voute et al. | |
| 2006/0272976 A1 * | 12/2006 | Pinney et al. ................. | 206/466 |
| 2009/0062755 A1 * | 3/2009 | Burgess et al. ............... | 604/326 |
| 2009/0325771 A1 | 12/2009 | Inoue et al. | |
| 2010/0315231 A1 | 12/2010 | Rada | |
| 2010/0318058 A1 * | 12/2010 | Schroder ....................... | 604/410 |
| 2011/0052101 A1 * | 3/2011 | Paulse ............................ | 383/23 |
| 2011/0059832 A1 * | 3/2011 | Giampieri et al. ............ | 493/186 |
| 2011/0135223 A1 * | 6/2011 | Suzuki et al. ................. | 383/114 |
| 2012/0310150 A1 * | 12/2012 | Brandl et al. .................. | 604/29 |

* cited by examiner

BAG WITH A FLEXURALLY RIGID PLASTIC PART WELDED INTO IT

BACKGROUND OF THE INVENTION

1. Field of Invention

The invention relates to the field of preparing medical solutions, in particular solutions for infusion and renal substitution therapy. The subject matter of the invention is a bag, in particular a multichamber bag for holding concentrates with a circumferential seal and a holding area made of a flexurally rigid material surrounding the feed ports and/or withdrawal ports for fluids.

2. Description of the Prior Art

Dialysis fluids for hemodialysis or peritoneal dialysis as well as fluids and replacement fluids for hemofiltration processes typically contain dissolved substances, for example:

electrolytes Na, K, Mg, Ca to maintain an acceptable electrolyte balance in the patient buffers (for example, bicarbonate, acetate, lactate, etc.)

glucose (or other osmotic agents) as osmotic agents in peritoneal dialysis or for maintaining the blood sugar level during hemodialysis and hemofiltration acids or salts of acids (for example, HCl and/or Cl$^-$, acetic acid and/or acetate, citric acid and/or citrate) which might contribute toward the neutralization of basic partial dialysis solutions or are present as counterions in electrochemical equilibrium.

The substances used for dialysis solutions cannot usually be stored in a ready-to-use mixture because these substances can cause mutual degradation. The required stability of a component in storage may presuppose storage conditions that would lead to degradation of other components. One example is glucose, which can be stored for a lengthy period of time only in a certain acidic pH range, depending on the concentration of the glucose in solution, without being subjected to unwanted degradation processes to an excessive extent. At the same time, the compound sodium bicarbonate, which is often used as a buffer in dialysis solutions, cannot be stored under such acidic conditions because, depending on the pH, bicarbonate tends to decompose and can release $CO_2$. Under decomposition conditions, the concentration of bicarbonate changes, which is unacceptable from a therapeutic standpoint. The rising $CO_2$ partial pressure also makes demands of the medical dialysis machines leading to technical problems.

A variety of alternative compositions, storage conditions and dosage forms of dialysis solutions or concentrates are known which permit long-term storage. It is known that the solution components are divided into a combination of partial solutions or concentrates so that only compatible components of a partial solution or of a partial concentrate are stored together. For the solutions used in peritoneal dialysis, a first partial solution comprising glucose, which assumes the function of the osmotic agent, is typically stored at an acidic pH together with additional electrolytes, for example, sodium, calcium, magnesium. Another basic or buffered partial solution is necessary to supply a physiological mixed solution or at least a mixed ready-to-use solution of the first part and the second part with the first acidic partial solution for treatment. The second part often consists of a solution or a concentrate of sodium bicarbonate and sodium chloride. The partial solutions or concentrates are present in several containers or in several compartments of one container. The partial solutions or partial concentrates are present separately, so that there is no mutual influence. Immediately prior to use of the dialysis solution, the separate partial solutions or partial concentrates are mixed, possibly with the addition of other aqueous components and are prepared for the treatment.

In hemodialysis, partial solutions or partial concentrates are often present in the dialysis machine and are mixed during the course of the treatment to prepare a finished dialysis solution. Partial concentrates in solid or liquid form are often used for this purpose; these concentrates are present in individual containers and are diluted by connection to the dialysis machine with the help of a prepared hydraulic solution and then are processed to yield the finished ready-to-use dialysis solution.

Other developments in dialysis have tended toward supplying the necessary concentrates in a single container. First, this simplifies the production and handling of the containers but secondly this also simplifies the hydraulic system of the dialysis machine because then only one holding unit for the partial solutions or concentrates need be provided and fewer connections are necessary to process the solution through the hydraulic system. This trend can be observed in particular in acute dialysis because a greater mobility of the treatment systems is demanded there.

In another variant, dialysis solutions for hemodialysis are not prepared from concentrates during the course of the treatment but instead the total required volume of the dialysis solution is prepared in one batch in a step prior to the treatment. The batch is stored in a tank which is prepared for connection to a dialysis machine. In many cases, the tank is an integral component of a dialysis treatment unit or in certain cases it may also be moved separately from the latter. Batch dialysis may thus offer the advantage that the treatment site can be selected relatively independently of location through the one-time preparation of the batch. Thus treatment stations at various locations can be used without having to rely on a dialysis solution preparation unit or a water connection which supplies the necessary water for diluting the concentrates. In these cases, the dialysis solution is mixed from concentrates on an apparatus provided for this purpose and then is stored, usually in a portable tank.

Large-volume liquid bags, which are understood below to be bags having a capacity of at least 5 liters, are subject to special mechanical requirements. The film material of the bags must have an impact strength that is high enough so that the bags will not rupture if they fall. These requirements are demanded at low temperatures in particular. Corresponding suitability tests have assessed the strength of solution bags in a fall test. In this test, bags first regulated at a temperature of 4° C. are dropped to the floor from a height of 2 meters in a room regulated accordingly and any rupture behavior of the bags that occurs is evaluated. In addition, the welds of the bags which are assembled from film sections must be able to withstand certain compressive stresses without resulting in leakage of the bag. The bag materials must also meet additional requirements of heat sterilizability and transparency. These requirements are relevant for solution bags in particular which are marketed and distributed in sterilized and ready-to-use form. The mechanical stresses to which such bags are exposed on the distribution routes result in complaints and unpleasant follow-up demands on the part of customers to the manufacturers. Solution bags for peritoneal dialysis, hemodialysis and hemofiltration are conventionally available in sizes of up to five liters.

It is still difficult to supply large-volume solution bags in a ready-to-use form because of the transportation logistics. For bags which are used in batch dialysis as described above, the solutions must be prepared at the treatment site and at the site of use. The bags must thus be filled on-site by a suitable fluid processing installation and can be used within the hospital ward, and to a certain extent also regionally beyond that. Such batch systems may require bag volumes of 30 to 120 liters. Such large-volume bags already have a heavy load on welded sections, e.g., the welded seams or ports welded into the bags, due to their inherent weight.

To be able to fill or empty a bag through a port, these ports must be incorporated into the circumferential weld which secures the film wall sections against one another and defines an internal volume of the bag. The ports have a through-opening connecting the inside of the bag to the outer area so that fluid can flow through it. The outer end of the port is connected to additional lines or connections of the bag system of the treatment station. It is known that the welded area of the ports should be designed in particular for the welded connection to the film material. Therefore so-called welding ribs have been developed, running the transverse direction to the direction of extent of the through-opening of the ports and running parallel with the weld of the film. During the manufacturing process, welding tools press the films against these relatively thin welding ribs, resulting in a very high contact pressure locally, which seals the weld.

Beyond the simple sealing, however, these joints must also establish a fixed mechanical connection between the film and the port. It is customary in many cases for the bag to be supported by means of holders at the welded ports or in a suspended position. Depending on the volume of the respective filled bag, the film exerts high tensile forces on the weld due to the gravitational force of the material forming the filling. For large-volume bags, the technical requirements for establishing the described weld in a sealing and load-bearing manner would be too high to manufacture a bag system with acceptable manufacturing costs in mass production.

The tensile forces acting on the film walls due to the gravitational force and possibly the internal hydrostatic pressure of a filled large-volume bag on the film walls may lead to thinning of the film material. The film wall yields to the tensile forces because of plastic or elastic deformation. Films may be designed to be stable accordingly despite these deformations. Reference is made in particular to WO 2011/128185, the content of which is herewith referenced explicitly. This document describes an elastically extensible film which is provided for producing a large-volume bag.

One problem that occurs in mechanical stressing of welded sections on large-volume bags, is that the film may become detached from its welded connection with the welding ribs of the welding boat due to thinning. Such an effect may occur in particular because the film material must be stretched over the curved welding ribs of the welding boat for the welding operation. In addition, film-stretching forces also act on this welded location due to the force of gravity or the hydrostatic pressure of the filled bag.

It is also desirable for such plastic parts to have functional designs such as holding sections for access ports to the bag or a holding device to which the bag can be attached. These use requirements also necessitate the use of a mechanically stable, flexurally rigid material.

EP 1 554 177 discloses a method for sealing and welding tubing ports in place between the film walls of the solution bag. This document refers to mechanical gripping of the film, insertion of the tube port and then welding. The problems of film elongation are discussed, but this document does disclose a plastic part made of a flexurally rigid material.

EP 1 438 090 discloses bag having two access ports, each of which opens into two separate internal areas of the bag. The bag has a holder consisting of simple receiving holes in the film material. Such a holding device is not suitable for large-volume bags because the film material can tear under the load of the filled bag.

EP 1 642 614 B1 discloses a concentrate bag with a plastic part, which is prepared functionally for adding/removing fluid and which assumes the holder function of the bag. The plastic part is welded to the film walls in a sealing manner via welding ribs. The bag holds a concentrate for preparing a saturated solution, with which a dialysis fluid can be prepared. On the whole, the bag has only a low weight, even in the filled state, so that the problems of ensuring the sealing function and holding function of the welding zone of the welded hard part are not important.

U.S. Pat. No. 4,386,634 discloses a large-volume container in which dry concentrates are placed for preparing a dialysis solution. A liquid concentrate is prepared by adding water. The embodiment of the connection between the film wall and the hard part is not described in detail from the standpoint of the fastening and sealing.

SUMMARY OF THE INVENTION

The object of the present invention is therefore to create a bag which can withstand mechanical loads in the area of the inlet lines and outlet lines, such that the bag at the same time ensures a high safety for sealing storage of the material filling the bag.

DESCRIPTION OF THE INVENTION

This object is achieved by the subject matter described herein, which is a bag for holding a medical fluid, in particular a ready-to-use and/or spent fluid such as that which occurs in extracorporeal blood treatment or renal therapy, and a method for producing a bag. Advantageous embodiments are represented by the features of also described herein.

This object is achieved in particular by a flexurally rigid plastic part, which is connected to the film walls separately from the bordering line.

This in one process for producing a bag, an inlet or outlet port is connected with a seal to the film walls in a bordering line of the bag to be produced. In a separate area from this sealing welded area, a flexurally rigid plastic part is connected to the film walls to form a mechanically load-bearing connecting zone directed at the mechanical claims of the bag.

The bag according to the invention is constructed of film wall sections. The walls of the bag are preferably made completely of film materials. The film material is characterized in the sense of the present inventive teaching in that it is a thin, flat, flexible elastic material. Such flat plastic materials which are present in tubular form that can be placed flatly on a surface are also covered by this concept. Layer thicknesses of the films used for the inventive subject matter are within the range of 50 to 500 μm, in particular 80 to 300 μm, depending on the design also in the range of 100 to 250 μm. The term "bag" in the sense of the inventive teaching comprises collapsible containers which are in a flattened form when empty due to their inherent weight. The term bag also comprises embodiments in which parts of the bag walls are prepared of a flexurally rigid material as long as the bag can be folded up when empty in its overall character.

It is characteristic of an inventive embodiment that at least two films form an inner enclosed volume along a shared bordering line and thereby form a bag. The bordering line may be a peripheral weld connecting two films placed one above the other. However, the bordering line may also be understood to mean that it consists of welds of the films only in some sections but in other sections forms a folded film. This is the case with tubular films in particular. Such films are placed flatly so that the two film tube halves are placed one above the other and form a film fold at least at the sides, this also being understood to be a bordering line. In additional areas, the loose ends of the films must be welded to obtain a closed bag. Access ports are created between the films. For example, tube sections may be inserted between two films and welded or glued in place forming a seal in the common bordering line of the at least two films, as illustrated in EP 1 554 177. Alternatively, the ports may also be formed from flexurally rigid material containing the welding ribs and may be welded into the shared bordering line of the films so as to form a seal.

The ports fulfill the function of establishing access to the inner bag volume and the outer area. They may be connected to additional fluid guidance means, e.g., tubes, connectors and adaptors in order to ensure a fluid supply or fluid withdrawal.

In addition, the bag according to the invention is characterized by at least one flexurally rigid plastic part formed in the bag and designed to integrally accommodate the at least one feed/withdrawal port. The term "flexurally rigid" in this context is understood to mean that an object cannot be deformed geometrically without destroying the functional orientation.

Flexurally rigid plastics in particular are understood to be thermoplastic materials which are used at a temperature below their Vicat temperature according to ISO 306. The flexurally rigid plastic part is joined to the bag or the film walls; this is to be understood as meaning that the plastic part is welded, bonded or joined to the films by a clamping action. Additional fastening methods may be considered as being equivalent if they yield a load-bearing connection in the mechanical connection to the film walls. It is provided in particular that the bag may be connected to the fastening system or a restraint system by means of the incorporated plastic part. This presupposes that the connection between the flexurally rigid plastic part and the film wall of the bag must be so stable that the bag can be stored in a suspended or partially suspended manner, for example.

In particular it has been found that port accesses which form a seal and are incorporated into the peripheral line of the bag and a flexurally plastic part incorporated additionally for mechanical fastening and/or restraint of the bag are advantageously joined to the film walls of the bag by separate connecting areas. This makes it possible to ensure that the sealing areas of the peripheral line around the access port are exposed only to the mechanical stress due to the hydrostatic filling pressure. However, the sealing areas are not exposed to the mechanical stresses due to tensile forces of the film on the sealing areas which occur, for example, due to a suspended storage of the bag. The connection between the flexurally rigid plastic part and the film walls then need not be created so precisely that it fulfills a sealing function, which is an advantage, and such an imperviousness is preserved even with suspended storage and with the resulting tensile forces on these joining areas.

In one embodiment the access port or additional ports, e.g., vent ports are incorporated into the peripheral line by welding/gluing. Film sections protruding beyond this peripheral line may be welded, clamped or glued to the flexurally rigid plastic part so that the sealing area and the restraint area act on different zones of the bag.

The flexurally rigid plastic part may comprise additional functional units. It may be prepared to receive another access port to direct additional fluids to the interior of the bag or to enable venting/aerating of the bag in withdrawing or adding fluids. In this case, each access port may be equipped with a septum, for example, in order to be able to supply additional components of the stored dialysis fluid by means of syringes. In addition, hydrophobic filters may also be included by the access ports for sterile venting and filling of the bag.

Welding methods are recommended as the preferred method for producing joints between the bag film and the ports. Although similar joining effects of the bag components might be achievable through adhesive bonding, welding is preferred from a technical production standpoint. Welding of the tubular access ports into the peripheral line of the bag is also preferably performed by welding methods. Welding methods are understood to also include laser beam welding methods such as those mentioned in WO 2007/115803. Likewise, reference can also be made to the techniques of EP 1 554 177 for welding the ports in place.

The separation of the sealing welds of the ports and the welding of the functional flexurally rigid plastic part are relevant in particular for bags with a large capacity. Bags having a volume of five liters that are filled with dialysis fluid are offered in the dialysis field in particular. When these bags are hung at the site of treatment of the patient, the film material is subjected to extremely high mechanical stresses due to the inherent weight of the filled bag. The object according to the invention is thus relevant in particular for bag sizes of more than two liters, such as those used in peritoneal dialysis, for example. This is also relevant for five-liter bag sizes, which are used for dialysis fluids or replacement fluids in peritoneal dialysis, hemodialysis or hemofiltration. There are known concepts in dialysis for supplying bag sizes of up to 500 liters for supplying multiple dialysis treatment stations with dialysis fluid centrally. In acute dialysis, bag volumes of up to 120 liters may be provided, these bags being stored in a portable tank to be connected to a dialysis treatment station. In particular a bag with separate welding of the sealing peripheral line and flexurally rigid plastic part is relevant for bags in a size of 5 to 120 liters. Bag sizes with a capacity of 30 to 90 liters, especially preferably 45 to 75 liters are preferred.

The technical advantage of separate welding of ports in the sealing peripheral line and accommodating the ports in the separately welded flexurally rigid plastic part is manifested in a bag in particular when the bag is designed as a multichamber bag. In this case, a port may connect the internal area of a chamber with the external area of the bag and in this way a plurality of ports may be accommodated by the flexurally rigid plastic part welded into the bag. Chambers may be designed differently. In one embodiment, a chamber is formed from an inner bag and a bag surrounding the inner bag in turn forms two additional chambers. There is also the possibility that the inner chamber or the outer chambers are in turn subdivided into compartments. The compartments are divided by bordering lines which preferably consist of welds. In another preferred embodiment, the bordering lines consist of peel seams in at least some sections.

In this context, peelable welded connections are understood to be joining sites of two joint partners exerting an adhesive effect on one another due to the heat treatment. In the present case the joining partners are two opposing film pieces of a bag which are joined together in the welding process in welding jaws by the action of heat and contact pressure. The welding temperature determines the force with which the peel seam can be opened. A peel seam is understood to be an adhesive bond which can be released again by the application of force without resulting in a complete tearing of the film material. In special embodiments, a peel joint may also be understood to refer to a connection which causes partial delamination of a multilayer film laminate when a force is applied. In these cases, it is important that the delamination tear does not cause complete rupture of the film material, which would make the bag unusable.

The welded flexurally rigid plastic part is preferably prepared so that it is able to receive multiple ports, each of which establishes a connection to multiple chambers or compartments of the bag. Thus this yields the advantage that a plurality of the ports is combined on one plastic bag. This advantage is manifested in particular when the bag is secured by means of the plastic part in a restraint and the ports are to be connected to additional fluid-conducting means, e.g., tubing, adapters, etc. In particular the flexurally rigid plastic part may advantageously integrate additional functions in all embodiments; for example, restraints for additional objects, e.g., tubing may be provided. Furthermore, sections of the plastic part may be separated by a parting line so that a section of the plastic part can be broken off to show that the bag has already been used.

For the connecting area between the film walls and the flexurally rigid plastic part, it is not necessary for this connection to be designed as a sealing connection. From the standpoint of production technology it is advantageous only to be sure that this connection, e.g., a welded, glued or clamped connection, is designed to be so stable that it can absorb all the mechanical forces due to the load of the filled bag. This refers in particular to such forces which act in fastening the bag by means of the flexurally rigid plastic part. A fastening for the bag may appear so that the bag is supported in a freely suspended position and is carried by means of the hard plastic part welded into the bag. The hard plastic part is therefore equipped with eyes or a retaining rail, which engages with complementary retaining devices. The advantage of integrating retaining elements into the flexurally rigid plastic part is in particular that of designing it in an asymmetrical form. The retaining elements of the bag and the complementary retaining device to hold the bag may thus be brought into retaining engagement only in a certain relationship. This ensures that improper fastening or improper connection of the bag in the connecting parts of the dialysis treatment station is rendered impossible.

With very large bags, a supporting apparatus is also provided in addition to the restraint by means of the flexurally rigid plastic part welded into the bag, and surrounds and supports the bag in at least some sections in order to reduce the forces acting on the connection between the film walls and the flexurally rigid welded part.

A film material which is elastically extensible is advantageously used by the bag in a large-volume embodiment between 5 liters and 120 liters. In filling the bag, the capacity of the bag increases with an increase in the filling, much like inflating a balloon. The use of such elastically extensible film materials has the advantage for large-volume bags that a large capacity of the filled bag can be made available using less film material. It is thus also possible for the bag to have a volume of five liters in the unextended state and to have a volume of 60 liters in the filled state. A film material which may preferably be used here is that described in WO 2011/128185, to which reference is herewith made explicitly in all details.

The object according to the invention is especially important in the design of bags with extensible film material. The extension of the bag causes thinning of the films. The choice of such film materials therefore requires higher precision in the execution of the sealing weld. To this extent, it is especially difficult to design a weld to be mechanically load-bearing and sealing at the same time. Therefore, according to the invention, welded areas which assume a sealing function are separated from welded areas responsible for the mechanical restraint of the bag.

In some embodiments, it is possible to use the non-sealing welded area for additional functions besides the above-mentioned holding of the flexurally rigid plastic part. It is provided in particular in one embodiment that an information carrier is joined by welding or gluing or clamping to the area forming the connection between the flexurally rigid plastic part and the film sections. The information carrier may be embodied as a printed film piece which provides information about the bag and the product contained in the bag. The information carrier may contain machine-readable information, which can be processed optically or magnetically or inductively by means of a reader. Examples of optical information transmission include machine-readable barcodes or pixel codes, e.g., dot matrix codes, as well as color codes and the like. Magnetic transmission may be accomplished by output of information on magnetic strips. Inductive information transmission according to the RFID technique, which may also be associated with the bag in one embodiment on the information carrier, this is also known. In another embodiment, the information carrier is connected to the bag and/or to the non-sealing area between films and flexurally rigid plastic part by detachable means. Detachable means may include for example, perforated film sections which allow the information carrier to be detached. Alternatively, the film type information carrier is connected to the bag by a peel connection. In this case the information carrier may also be arranged separately from the non-sealing connecting area.

The object according to the invention also comprises a method for producing a bag, wherein sealing welded areas and mechanically load-bearing welded areas are separated from one another. In the method according to the invention, flat films are placed one above the other in parallel and are joined to one another by welding or gluing along a peripheral line. Welding methods are preferred for use here. If the bag is constructed on the basis of tubular films, then a flattened film tube is used to produce the bag so that an upper film section is parallel and opposite a lower section. To produce the peripheral line the film tube then need not be welded or glued at the sides. In this case the film fold formed in the flattened state forms a section of the peripheral line.

Then the port accesses are positioned between the films to be joined, preferably using tube ports. With the production of the connecting peripheral line of the two films, the tube ports are installed with a seal in the peripheral line. For example, ultrasonic welding, mirror welding, contact welding or laser beam welding is used to produce the sealing peripheral line with the ports incorporated.

In another step, the flexurally rigid plastic part is connected to film sections of the bag. To do so, a protruding film section is used in the area where the ports are integrated into the peripheral line. The plastic part is connected to the protruding film sections and this may be accomplished by means of welding techniques, gluing techniques or by clamping. The preferred joining methods include welding methods. The plastic part may be located in immediate proximity to the peripheral line in which the ports are enclosed with a seal.

The flexurally rigid plastic part may be prepared for receiving the port to be welded in situ. For example, one or more ports may be inserted into hollow passages in the plastic part. The connection between the port and the receptacle on the flexurally rigid plastic part may be accomplished by gluing, heat blocking or welding, in particular by laser beam welding. Heat blocking is a method of bonding the materials of the tube port and flexurally rigid plastic part under the influence of heat. In particular, "receiving the ports on the flexurally rigid plastic part" is also understood to mean that the port and the flexurally rigid plastic part form an integral component. The port sections themselves may be made of the material of the flexurally rigid plastic part.

In one embodiment, the port receiving area on the flexurally rigid plastic part may comprise a septum to form an inlet port that can be punctured with a needle. Another receptacle area may contain a filter, in particular a hydrophobic filter to vent the bag in an almost sterile manner when filling the bag or withdrawing fluid. The filter is designed as a sterile filter which effectively excludes the transport of microorganisms or endotoxins.

Although this describes a sequence of production steps which describe the object according to the invention, it must be regarded as completely equivalent to have the production steps conducted in a different sequence. In particular it does not matter whether the ports are first connected to the film sections of the bag and then connected to the receptacle areas of the flexurally rigid plastic part or vice versa. In the latter case, the tube ports are connected in a first step to the receptacle area on the flexurally rigid plastic by adhesive bonding, blocking or welding. In another step, this assembled part is welded to the film material. In doing so, the assembled part is positioned with the port ends between the layers of film placed one above the other. Next the production step takes place, in which the flexurally rigid plastic part is joined to the films, or the sealing peripheral line which seals the port(s) is produced first.

From a technical production standpoint, it is preferable if the connecting areas between the flexurally rigid plastic material and the films are not designed to be sealing. A sealing connection, e.g., a welded connection requires a high manufacturing precision. The film sections must be stretched accurately to surround hard parts or tube ports that are to be welded into curved surfaces so that a seal is formed. For this reason, it is sufficient if the welded connection between the flexurally rigid plastic part and the film is used only in those sections in which welding which is not associated with any stretching of the material can be performed rapidly. Therefore only planar surfaces of the film wall and the plastic hard part and those that are aligned in parallel are welded. The receptacle areas of the ports in the plastic part are preferably excluded from the welding.

The method according to the invention may of course also be used for multichamber bags, in particular also for so-called "bag-in-bag" constructions in which an inner bag defines a first capacity and an outer bag, i.e., a bag surrounding the inner bag, forms a second capacity and optionally a third capacity. In this case, it is assumed that four films layered one above the other are used, such that the lower film may also be understood to be half of a tubular film. This concept is also to be understood to mean that two flattened tubular films placed one inside the other would yield a sequence of four layers of film placed one above the other. Likewise a flattened tubular film and two individual films would yield a sequence of four films. In another step the ports are positioned between the films in such a way that they are already assigned to the chamber area of the finished bag. Thus one port can be positioned between the first and second film or between the second and third film or between the third and fourth film. Next, as described previously, the sealing peripheral lines are designed with the ports sealed in them so that in this area the four films and the respective port are joined by the shared peripheral line. Therefore this yields a bag having a plurality of chambers and, depending on the respective embodiment desired, each chamber is provided with a port access.

With the embodiment of the peripheral line or the connection, another functional film piece can be connected between the plastic part and the film walls. At such locations, it has proven to be advantageous to apply an information carrier containing information about the product in legible form or in a machine-readable form. In particular when a bag having an elastically stretchable film is used, regions of the bag cannot be printed with legible information because the print image would be destroyed when the bag is filled and the films are stretched. It has therefore proven necessary to apply the information carrier to the bag separately, so that the stretching of the film cannot have any effect on it. In particular an applied film containing information, e.g., in written form, as a barcode, as a dot matrix code, as a magnetic strip or an RFID chip may be provided on the front and back sides. The connection of the peripheral line or to the connecting area between the plastic part and the film wall may be peelable or may consist of an adhesive bond so that the information carrier can be removed and a patient file for example, can be inserted into a treatment record.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit, and scope of the invention will become apparent to those skilled in the art from this detailed description.

Figure 1:
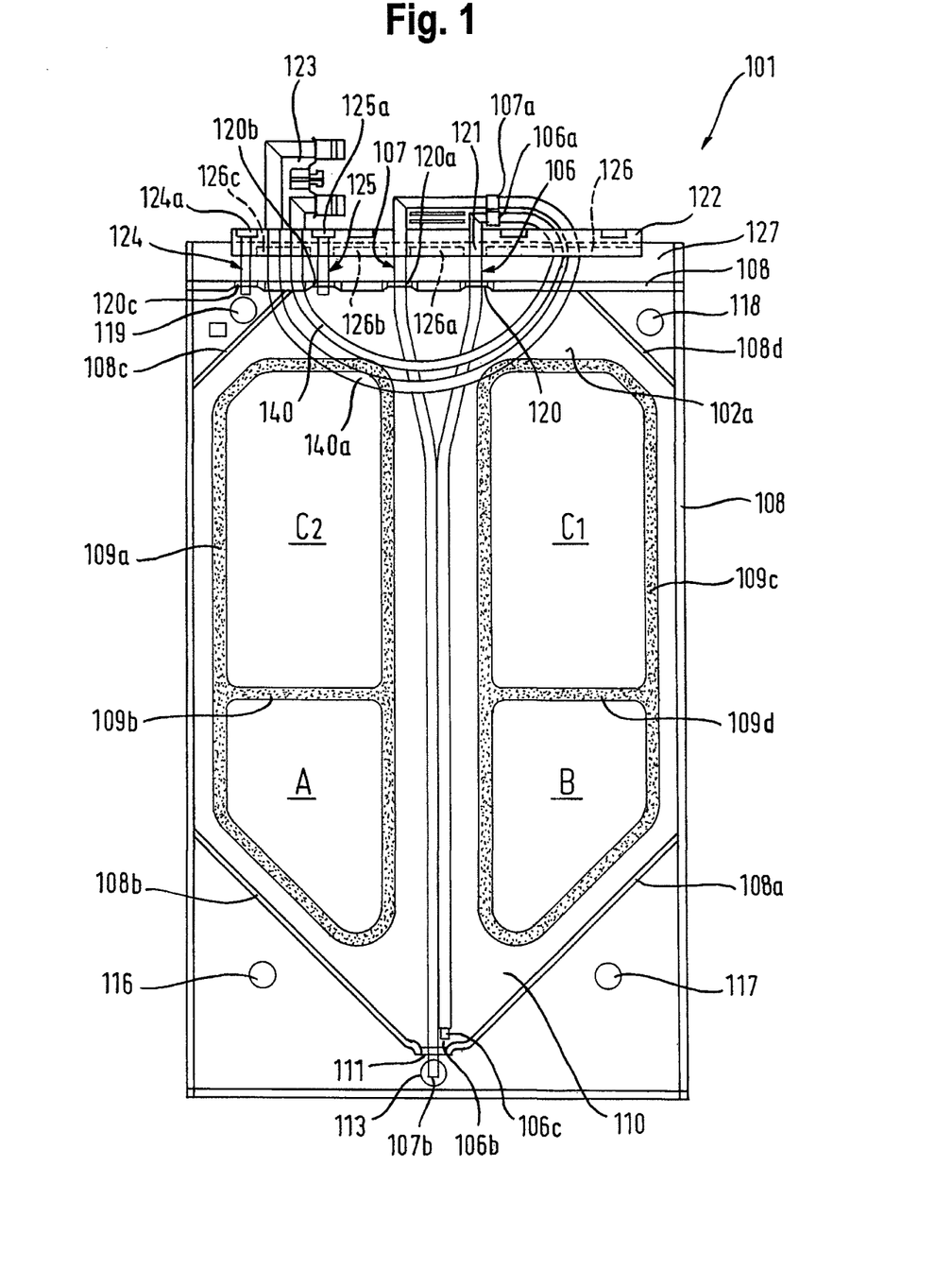
FIG. 1 shows a schematic view of a bag according to the invention, in particular a multichamber bag having ports accommodated with a seal in the peripheral line and having a flexurally rigid plastic part incorporated separately thereof.

The bag shows, as illustrated schematically in FIG. 1, an upper outer wall 102*a* and a lower outer wall 102*b* (not shown) which are bordered by a joint peripheral edge 108 and are joined in a fluid-tight manner. In a preferred version 102*a* and 102*b* are the upper and lower films of a bag and the sealing peripheral lines 108 are formed by a joint permanent weld.

The bag has a first compartment A and an additional compartment C2 which are filled with concentrates for preparing dialysis fluids. The compartments A and C2 are enclosed along a closed peripheral line by a dividing line 109*a* which consists of a dividing line which is peelable in at least some sections in the embodiment shown here. The contents of the compartments A and C1 are separated from one another by the additional dividing line 109*b*. The additional dividing line 109*b* may consist of a permanent welded line, a partially semipermanent welded line or a peel seam. The dividing lines 109*a* and 109*b* are preferably embodied as peel seams and form a cohesive integral construction of peel seam sections.

The exemplary embodiment according to FIG. 1 is also characterized in that a connecting port 106 connects the filling chamber 110 of the bag to the exterior of the bag via a first end in the interior of the bag 106*b* and an additional end 106*a* outside of the bag 101. Port 106 is preferably attached to the welded zone 120 by welded joints in a fluid-tight manner in the sealing peripheral line 108. In addition, port 106 is accommodated by the receptacle area 121 of the flexurally rigid plastic part 122 by welding, gluing or blocking with a seal. Means 106 are preferably provided at the end 106b of the port 106 to produce fluid turbulence in the inflowing diluent. These means may be embodied as a turbulence-generating nozzle or as a turbulence-generating frit. In addition, port 106 consists of a tube passing through the bag in the interior in its longitudinal extent. Thus it is ensured in the filling process that when the bag is stored upright, for example, by accommodating the bag on a retaining rail through the flexurally rigid plastic part 122, the bag is filled from beneath and the compartments A, B, C1, C2 are opened in the sequence A simultaneously with B, before C1 and C2 due to the inner filling pressure.

Another port 107 with a first end 107a outside of the bag and another end 107b serves to return spent medical fluid, preferably spent dialysis solution, to another chamber of the bag system. Port 107 here is designed as a tube in the interior of the bag and is provided for passing through the bag along a longitudinal extent when the bag is stored in a hanging position, for example, by accommodating the bag on a retaining rail of the flexurally rigid plastic part 122. In the welding zone 111, the tube 107 passes through the peripheral line 108a of the bag 101 and opens into another chamber (not shown). The zone 111 may be a fluid-tight welded location which secures the bag between the upper and lower bordering planes 102a and 102b and is part of the welded peripheral line 108. The chamber (not shown) is a sheathing container, preferably a bag which is an integral component of the container system 101. This results in a "bag-in-bag" construction in which the bag holding the ready-to-use fluid is sheathed by a bag holding the spent fluid.

In addition, the embodiment in FIG. 1 shows a set of concentrate chambers B, C1 which are surrounded by another dividing line along a closed peripheral line 109c. Another dividing line 109d separates the contents of the concentrate chambers B and C2. In a preferred embodiment the lines 109c and 109d which are embodied as peel seams form an integral construction of peel seam sections developing one into the other.

In the exemplary embodiment, the compartment B contains a glucose concentrate in powdered and/or anhydrous form or in liquid form.

Another compartment C1 contains a concentrate, which is incompatible with the concentrate of the compartments A and B, i.e., has a tendency to degradation or would cause unwanted interactions.

This embodiment also shows a peripheral line 108 which preferably consists of a permanent weld. Additional permanent weld lines, sections 108a and 108b, border the container contents or the bag contents, forming an inclined bottom of the interior space. This design facilitates the production of turbulence in the incoming flow of diluent due to the means 106c for generating fluid turbulence and thus facilitating the dissolving process of the concentrates out of the compartments A, B, C2 and C1. Bordering lines 108c and 108d impart additional stability to the field container, in particular the bag, in the filled state. This is important in particular for large-volume containers with which the internal pressure can exert a tension effect on the peripheral line 108 due to the quantities contained. Large-volume bags having a volume of 5 to 120 liters, 40 to 80 liters, in particular 60 liters±15%, are to be understood as containers in this sense.

In one embodiment, the filling chamber is filled through port 106, dissolving the concentrates from compartments A, B, C1, C2. To withdraw the prepared solution, the contents for dialysis therapy or other processes are removed by means of an external pumping means such as a rotary hose pump or a diaphragm pump. After using the fluid thereby removed, it is returned to the bag system through port 107 through recess 113 in the opposite films so that the end of the port is in fluid connection with the volume of the outer sheathing bag.

FIG. 1 also shows that the port ends 107a, 106a are connected to additional fluid guidance means, in this case the tubes 140, 140a. The tubes in turn have at their ends a connector part 123 which is provided for bringing the dialysis fluid into fluid connection with another fluid processing device such as a dialysis machine.

Vent ports are labeled as 124 and 125; 125 may be connected to the filling chamber 110 of the bag, for example, while port 124 is connected to the sheathing bag. When the chamber 110 of the bag 101 is filled through the port 106, excess air can escape through the vent port 125. When spent fluid is returned through port 107 into the sheathing bag (not shown here) the necessary venting may take place through port 124. The vent ports 124, 125 which pass through the sealing peripheral line to the sealing locations 120c and 120b are held by the flexurally rigid plastic part 122. The plastic part contains receiving areas for hydrophobic membranes 124a and 125a, so that the venting of the chambers may be accomplished under almost sterile conditions.

It is clear on the whole that four ports 106, 107, 124, 125 pass through the peripheral line 108 at the locations 120, 120a, 120b, 120c, forming a seal and are held by the flexurally rigid plastic part 122. The flexurally rigid plastic part itself is welded to the film 102a and to the film 102b (not shown) at the welded spots 126, 126a, 126b, 126c. As this shows, the welded zones are not permeable.

Through-openings in the film material of the inner bag are labeled as 116, 117, 118, 119 and should cause the surrounding bag to be filled uniformly when the surrounding bag (not shown) is filled with spent fluid through port 107 and opening 113.

Figure 2:
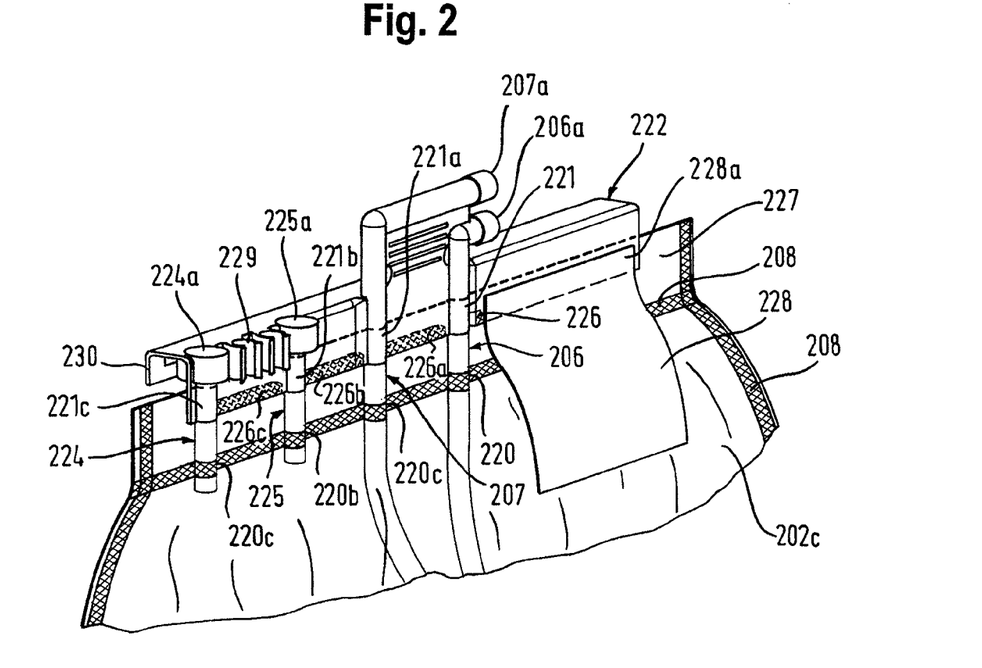
FIG. 2 shows another view in a lateral perspective of the bag.

FIG. 2 shows another diagram of the bag according to the invention. The outer bag is shown in this diagram. The bag system comprising the inner bag and the outer bag is in a partially filled condition. This diagram shows an upper film 202c which together with the rear film 202d and the connection along the peripheral line 208 define a closed capacity of the surrounding bag. The accesses to the interior of the outer bag and to the interior of the inner bag (not shown) are established through ports 206, 207, 225, 224. The ports 206, 207 are fluid ports for filling and withdrawing fluid. The ports 225 and 224 are accesses for sterile filling and venting during the filling and withdrawal processes. Port 206 supplies the access to the inner bag, port 207 supplies the access to the outer bag surrounding the inner bag. Similarly port 225 is a vent port for the inner bag and 224 is a port for venting the outer bag. These ports are incorporated into the peripheral line 208 at the locations 220, 220a, 220b, 220c and are accommodated by the flexurally rigid plastic part at the locations 221, 221a, 221b and 221c. The flexurally rigid plastic part is connected to the film section 227 protruding beyond the peripheral line 108 by welding for example. The port receiving areas 221, 221a, 221b, 221c are excluded from the welding.

FIG. 2 shows hose clips for receiving the hoses (not shown) which are connected to the port ends 207a, 206a. The corresponding tubes are labeled as 140, 140a in FIG. 1. The plastic part 222 is preferably manufactured in an injection molding method. It is therefore possible to integrate a plurality of functional units into the plastic part in one working operation of injection molding on the plastic part. In particular this also produces a plastic part having a U-shaped cross section due to the longitudinal extent of the plastic part. In this embodiment the plastic part is a U-shaped retaining rail as indicated by 230. The retaining rail may then be applied to a retaining device of a complementary shape and then the bag is secured in a receiving unit of a dialysis treatment station. In combination with the additional functional units of the plastic part, e.g., ports and hose clips, an asymmetrical design of the plastic part can be achieved with an appropriate arrangement. Asymmetrical in this context means that a mirror image of the plastic part cannot be formed to coincide with the original image by rotation and displacement. As shown in FIG. 2, geometric coding of the plastic part 222 can be established with which the bag and the plastic part can be attached to a restraining device in a manner not shown here only in an unambiguous manner. This is especially important for preventing faulty operation of the bag.

In FIG. 2 an information carrier is shown schematically and labeled as 228. This information carrier consists of a film-type material and is joined to the welded zone 226 on only one side via the connecting zone 228a. The film material can be printed and can be folded through the fastening, which is provided on only one side. The connecting zone 228a may be detachable, for example, if adhesive joints or blocking joints or peel seam joints are selected for 228.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A bag for holding medical fluids for renal therapy comprising film wall sections, which are welded together peripherally along a bordering line in at least some sections, having an access port with a first end that brings an inner area of the hag in fluid connection with an outer area and which is incorporated into the bordering line with a seal, and a flexurally rigid plastic part having a receptacle for the access port which is integrated therein, with the flexurally rigid plastic part being connected to the film walls separately from the bordering line, with the access port being welded into the bordering line, and with the flexurally rigid plastic part being connected to protruding film sections of the film walls by welding along a series of discrete points.

2. The bag according to claim 1, wherein the flexurally rigid plastic part has a receptacle area which is configured to receive the access port.

3. The bag according to claim 1, wherein the flexurally rigid plastic part includes an integral fastener that is at least one of a retaining rail and one or more vent ports.

4. The bag according to claim 3, wherein the flexurally rigid, plastic part is able to form an asymmetrical geometric shape with the integral fastener, so that the bag can be connected to a complementary restraint system only in one unambiguous way, and wherein the retaining rail has a U-shape.

5. The bag according to claim 1, wherein the bag is a large volume bag with a capacity of 5 to 120 liters.

6. The bag according to claim 5, wherein the bag has a capacity of 30 to 90 liters.

7. The bag according to claim 6, wherein the bag has a capacity of 45 to 75 liters.

8. The bag according to claim 1, wherein the bag is a multichamber bag.

9. The bag according to claim 8, wherein at least two chambers of the bag are each connected to an access port, each having one access port connected to the outer area of the bag, penetrating through the bordering line with a seal.

10. The bag according to claim 8, wherein the two access ports are each accommodated by the flexurally rigid plastic part.

11. The bag according to claim 1, wherein the film walls have a material of construction that is an elastically extensible material.

12. The bag according to claim 1, further comprising an information carrier that is fastened in the welded area of the flexurally rigid plastic part and the film wall.

13. A method of manufacturing a bag, comprising the steps of
placing at least two films one above the other or flattening a film tube,
positioning an access port between the films or between opposing film sections of the flattened film tube so that the access port is in proximity to opposing sides of films or film sections,
producing a sealing bordering line by welding the films or the film tube to the access port,
positioning a flexurally rigid plastic part having a receptacle for the access port which is integrated in an area between the part of the films or the film sections of the film tube protruding beyond the sealing bordering line, and
connecting the flexurally rigid plastic part to the protruding film sections separately from the sealing bordering line by welding along a series of discrete points.

14. The method according to claim 13, wherein the access port is attached to the material in a receiving area on the flexurally rigid plastic material.

15. The method according to claim 13, wherein the connection between the films or film sections and the flexurally rigid plastic part is not embodied to form a continuous seal.

16. The method according to claim 13, wherein four films are placed one above the other and are welded along a joint bordering line such that at least two opposing films may be formed from film sections of a flattened film tube to obtain a multichamber bag with an inner bag including an inner chamber, and a bag surrounding the inner bag including a second chamber and/or a third chamber.

17. The method according to claim 13, further comprising another film piece that is connected to a connecting line between the films or film sections and the flexurally rigid plastic part.

* * * * *